US011653984B1

(12) United States Patent
Brady et al.

(10) Patent No.: US 11,653,984 B1
(45) Date of Patent: May 23, 2023

(54) UNASSISTED ROBOTIC SURGERY EMPLOYING PARAMAGNETIC HALO METALLOFULLERENES AS MINIMALLY INVASIVE, PRECISION SCALPELS OR MICRONIZATION PARTICLES THROUGH MAGNETIC FIELD MANIPULATION AND TARGETED EXENTERATION PATTERNED BY PROGRAMMED 3D IMAGING USING NEEDLE OR MAGNETIC ENERGY ACCESS AND MICROELECTRONIC SEMICONDUCTING IN NON-STATIONARY WAFER-LESS SPACE

(71) Applicants: Terry Earl Brady, The Valley (AI); Anthony Lee Dellinger, Burlington, NC (US); Lowell Hughes, The Valley (AI); Melinda K. M. Goddard, The Valley (AI)

(72) Inventors: Terry Earl Brady, The Valley (AI); Anthony Lee Dellinger, Burlington, NC (US); Lowell Hughes, The Valley (AI); Melinda K. M. Goddard, The Valley (AI)

( * ) Notice: Subject to any disclaimer, the term of this patent is extended or adjusted under 35 U.S.C. 154(b) by 0 days.

(21) Appl. No.: 17/884,185

(22) Filed: Aug. 9, 2022

Related U.S. Application Data

(60) Provisional application No. 63/333,022, filed on Apr. 20, 2022.

(51) Int. Cl.
*A61B 5/055* (2006.01)
*A61B 34/20* (2016.01)
(Continued)

(52) U.S. Cl.
CPC ...... *A61B 34/20* (2016.02); *A61B 2034/2051* (2016.02); *A61K 9/00* (2013.01); *A61K 49/06* (2013.01)

(58) Field of Classification Search
CPC .. A61B 34/20; A61B 2034/2051; A61K 9/00; A61K 49/06
See application file for complete search history.

(56) References Cited

U.S. PATENT DOCUMENTS

2006/0057211 A1* 3/2006 Chorny .............. A61K 47/6923
623/1.42
2007/0196281 A1* 8/2007 Jin .................... A61K 41/0052
424/9.34

(Continued)

FOREIGN PATENT DOCUMENTS

WO WO-2009054958 A2 * 4/2009 ............ A61K 49/12

OTHER PUBLICATIONS

Fernandez-Pacheco et al. (J. Magn. Magn. Mater. 2007, 311, 318-322).*
Wust et al. (Int. J. Hyperthermia 2006, 22, 673-685).*
Khandhar et al. (J. Biomed. Mater. Res. A 2012, 100A, 728-737).*
Wang et al. (Biomacromolecules 2017, 18, 1029-1038).*
Kotitz et al. (J. Mag. Mag. Mater. 1999, 201, 102-104).*

(Continued)

*Primary Examiner* — Michael G. Hartley
*Assistant Examiner* — Melissa J Perreira

(57) ABSTRACT

Multi-angle radiographic imaging enables 3D visualization of internal surgical targets like solid-tumors, heart vessels, blocked glands or any bodily cavities like fallopian or Eustachian tubes for diagnostics and surgery planning. Those images are dimensionally precise and easily replicated as life-forms with 3D printing for exact modeling. The "negative" aspects of the images are the diseased tissues requiring excision, as in a solid-tumor example. Needle biopsies are routine and can be radiographically guided. Similarly, guided needle delivery of a magnetic surgical fluid containing fullerenes into a target site, such as a solid tumor is less invasive than laparoscopic techniques. Introducing an external magnetic field force can then be used to propel, rotate and maneuver fullerenes into cellular matter or into tissue. Without such external force from the external magnetic field, the suspension of nanoparticles remains harmless due to their atomic scale, inertia and intrinsic repulsion from contact with nearby matter. Notably, fullerenes are hydrophobic and can move freely in biologic space (or interstitially) including amongst water molecules without contact. However, if energized and propelled by a controlled external magnetic source, the nanoparticle could readily penetrate cells, tissues, bone, or biological material. In addition to magnetic launching of the nanoparticles, rotation of the fullerene particles would create millions of nanoscale abrasive structures that can grind down larger structures like tissues, organs, or bones. By example, oscillating or reciprocal computer-controlled magnetic forces in radiographically defined space would activate fullerenes, inducing momentum and rotation that can exenterate a tumor, while chemically cauterizing small feeding vessels for hemostatic control and absent any damage to nearby normal, non-target matter. Essentially, biological material targeted with magnetically manipulated fullerenes could be ablated with a microscopic "sharpness" unattainable with conventional instrumentation. Magnetic forces are mathematically articulated and understood in highly precise terms, wherein objects subject to magnetic energy are controllable regarding mass, force and velocity. After completion of the surgical procedure, the magnetic fullerene fluid can be aggregated and removed along with flushing of attendant debris with a syringe or similar instrument.

14 Claims, 3 Drawing Sheets

(51) Int. Cl.
*A61K 9/00* (2006.01)
*A61K 49/06* (2006.01)

(56) References Cited

U.S. PATENT DOCUMENTS

2011/0196187 A1* 8/2011 Ludwig .................. A61N 2/002
 600/12
2017/0268977 A1* 9/2017 Garcia .................. G01J 3/0205

OTHER PUBLICATIONS

Moreno-Vicente et al. (Carbon, 2018, 129, 750-757).*
Wilson (Electrochem. Soc. Interface 1999, 8, 24-28).*
Tereshchuk et al. (Phys. Rev. B 2012, 85, 195461-1 to 195461-8).*

* cited by examiner

UNASSISTED ROBOTIC SURGERY EMPLOYING PARAMAGNETIC HALO METALLOFULLERENES AS MINIMALLY INVASIVE, PRECISION SCALPELS OR MICRONIZATION PARTICLES THROUGH MAGNETIC FIELD MANIPULATION AND TARGETED EXENTERATION PATTERNED BY PROGRAMMED 3D IMAGING USING NEEDLE OR MAGNETIC ENERGY ACCESS AND MICROELECTRONIC SEMICONDUCTING IN NON-STATIONARY WAFER-LESS SPACE

TITLE OF THE INVENTION

Unassisted Robotic Surgery Employing Paramagnetic Halo Metallofullerenes as Minimally Invasive, Precision Scalpels or Micronization Particles through Magnetic Field Manipulation and Targeted Exenteration Patterned by Programmed 3D Imaging Using Needle or Magnetic Energy Access and Microelectronic Semiconducting in Non-stationary Wafer-less Space.

CROSS REFERENCE TO RELATED APPLICATION(S)

N/A

FIELD OF THE INVENTION

The present application is related to magnetic manipulation of individual, incompressible nanoscale objects, such as pristine fullerene molecules, functionalized fullerene derivatives, endohedral fullerene molecules, functionalized endohedral fullerene molecules, or nanoparticles, and more particularly, to a system and surgical method for manipulating nanoscale objects with defined precision and spatial geometry. Spatial manipulation includes longitudinal, lateral, and vertical movement of the object in space through a defined region with specific and variable force and momentum. In addition to multidimensional movement of the nanoscale object, the systems are designed to impart rotation, oscillation, spinning, vibration, pulsing, or rocking of the nanoscale object, as it is moved through or suspended in three-dimensional space with variable rotational speed and torque, broadly or infinitesimally. An external magnetic field is employed for the positioning and rotational methods of the nanoscale object. The object of the present invention is to perform surgical procedures using precision-guided nanoparticles as an alternative to open cavity, endoscopy/laparoscopy and robotically assisted surgery techniques. Specific applications may include otherwise inoperable excisions, such as nearly inaccessible glands—and solid tumors due to risks posed in their removal using traditional procedures, as well as a wide range of traditional procedures whenever less invasive methods could further reduce collateral trauma, shorten recovery times, and improve both patient and healthcare cost outcomes.

BACKGROUND OF THE INVENTION

As the practice of surgery progressed into a specific discipline, incisions were made in various sizes using an evolving array of scalpels and more recently, lasers. Traditionally, surgical interventions have been employed to treat injury, deformity and disease using various implements over time. It is typically performed to initiate healing by removing diseased tissue and organs, tumors and obstructions, and/or resurfacing tissues, rather than as a therapy or cure, per se. Notably, the term "ectomy" describes the removal of particular tissues or organs (e.g., tonsillectomy, thyroidectomy, hysterectomy, prostatectomy) and accounts for the majority of routine surgeries.

Most surgical procedures can nonetheless impact healthy tissue and biologic and neurological homeostasis with long-term, negative effects. The latter include diminished patient quality of life—and lifespan—as a result of multiple procedures requiring lengthy anesthetization, as well as long recoveries. As such, improving methods to reduce trauma and shorten both procedures and recovery across a broad spectrum of procedures could ultimately enhance wellbeing and save millions in healthcare costs in both general and geriatric populations. Whether to insert hands and/or instruments or to allow for access and visualization of the target anatomy, practitioners have thus sought to minimize the impact on adjacent tissues and organs, as well as the patient overall.

Thus, surgical methods and instrument advances have focused largely on minimizing invasiveness and improving outcomes. These have included endoscopic, laparoscopic, laser, and robotically assisted instrumentation methods, however, these remain invasive techniques with attendant risks. These include both trauma to healthy organs and tissues from their use, as well as posing procedural limitations to the surgeon's dexterity and/or visualization of the site whether "hands-on" or with robotic assistance. Along this continuum, the reduction of physical impacts can diminish post-surgical complications and attendant pain, and thereby shorten recovery time and lengths of stay. Specifically with respect to smaller incisions, benefits may include prevention or lessening of cosmetic disfiguration and associated negative psychological effects, with overall improved quality of life.

In particular, the development of endoscopy and especially the single trocar technique to reduce the size and number of requisite incisions has improved outcomes, yet these remain constrained within the bounds of the surgeon's skills. Another such advance, heart valve replacement via vascular access, eliminated both extracorporeal oxygenation requirements and open-heart cavity trauma. Gaining access to the anatomy and engineering permanent placement of the substitute valve without healthy tissue injury or prolonged anesthesia were also breakthroughs in this discipline.

Nonetheless, these methods have posed disadvantages from reduced procedural space; shorter fields of vision; diminished tactile feedback; loss of stereopsis (depth perception); and constrained hand-eye coordination. Lengthy learning curves and training, as well as longer operations, have also increased the incidence of surgeon fatigue, higher procedural costs and deleterious sequelae due to prolonged anesthesia.

Advances in laser technologies have also enabled minimally invasive delivery of continuous or pulsed radiation, down to femtoseconds that could achieve unmatched precision while avoiding secondary tissue trauma in "bloodless" procedures with relatively rapid recovery. The primary mechanism of laser surgery is associated with thermolysis, or thermal decomposition, an endothermic chemical reaction from exposure to targeted radiation. Using both "wand" and fiber optic techniques, laser methods can achieve greater precision than typical scalpel manipulation. Laser interactions with biological tissue are generally characterized by scattering, reflection, and absorption. Depending on the type of laser and exposure duration, lasers can cause irreversible cellular damage in temperatures ranging from 45° C. (113° F.) to 60° C. (140° F.). Although lasers can penetrate from a thin layer of skin to deeper interstitial tissues, as well as being channeled through fiber optics, some risks to normal tissue and healthy cells surrounding surgical targets remain.

Innovations in the fields of imaging and computer science, such as high-definition optics, artificial intelligence and robotics have contributed to further advancing minimally invasive techniques. These have especially enabled real-time intraoperative imaging to compensate for perceptual disadvantages associated with smaller incisions and entry portals.

Herein, the proposed invention benefits from continuing advances in imaging technology. MRI and positron emission tomography (PET) have long augmented even the most skilled palpation assessments, x-rays from the turn of the last century, to the ultrasound techniques of the 1940s, and computed tomography (CT) methods adopted in the 1970s. First employed for preoperative imaging, all of these technologies have aided physician planning and modelling of procedures.

As these tools have enabled internal visualization of patient anatomy, they have expanded utility from pre-surgical images to real-time intraoperative guidance systems supported by computerization and video capabilities in the operating room. Today, an array of imaging tools, are routinely integrated to aid surgeons with both graphical base layers and real-time intraoperative overlays. Advances in artificial intelligence and diagnostics have also enabled enhancements such as coloration for differentiation of normal and diseased organs and tissues.

Real-time and preprogrammed navigation have made significant contributions to this discipline by reducing inadequate resections, as well as collateral tissue damage. Intraoperative modalities include optical (i.e., fluorescence and Raman), acoustic (i.e., photo-acoustics and radiofrequency-acoustics), and nuclear imaging. In particular, real-time fluorescence has enjoyed extensive market penetration due to ease of operation, acceptable sensitivity, absence of radiation, and cost effectiveness of the method. More than a dozen FDA-approved fluorescence imaging systems are now offered for routine use by market leaders, including Zeiss, Leica, and Intuitive Surgical.

Most recently, endoscopy dependent, robot-assisted methods have made further contributions to minimally invasive surgery. The inclusion of robotics has enabled consistent, smooth procedures with less fatigue, benefiting surgeons and patients alike. However, robot-assisted surgery is often slower than other methods, extending anesthesia and procedure times, along with attendant surgical risks. Longer setup and procedures associated with robotic surgery have also driven investments in modified scheduling logistics and operating room architectural design. Despite such improvements and trade-offs, extensive analyses have documented only narrow patient outcomes advantages compared to traditional procedures, which has slowed the adoption of robotic surgery (~1.5 million cases worldwide 2021; Xue et al., 2022).

Advanced modalities also include ultrasound use for needle biopsies as an example of tissue excision, resurfacing or removal in an ever-expanding practice of "invasive radiology." By merging this and other discreet disciplines based on imaging reliability, these advances have provided a framework for fullerene magnetic surgical procedures.

That said, the fundamentals that have driven innovations in minimally invasive surgical procedures are only intensifying with aging populations and recent declines in birth rates—adding risk to every procedure in a patient's life. Key variables in the progression have remained: human dexterity, accuracy and precision of automated instruments, and scale; whereby even the most skilled microsurgeon functions in galactic proportions relative to the cellular nuances of the tissues targeted in a given procedure. Indeed, the most common surgical instrument, the scalpel, is millions of times larger than each of the cells comprising the site of an incision.

With respect to scale, nanotechnology applications have also contributed to improved surgical instrumentation and delivery tools. For example, nanocoated surgical blades containing diamond nanolayers with low friction coefficients can decrease required penetration force, and 200-300 nm (nanometer) diameter needles have been used to penetrate and deliver molecules into the nuclei of live cells. The use of nanoparticles in surgery has also been proven with nano-photo-thermal-lysis, which applies a variety of nanoparticles with unique properties that improve target selectivity, accuracy, and lower required laser energies, thus enabling even less invasive surgical methods. Notably, the hydrophobic halo metallofullerene is capable of occupying space distinct and separate from other matter, possessing a slight interatomic wobble. The fullerene is thus unaffected by gravity, unpressurized fluidics or osmotic pressure at the atomic scale. Thus, a fullerene is a physically inert particle that remains biologically harmless in the absence of external forces.

Magnetism and the magnetic properties of materials have also been defined on the macroscopic level and at the quantum level with mathematical predictability. Magnetic levitation has been applied in various industries; whereby, magnets have been used to levitate and propel 30-ton trains in transportation—and applied to molecular applications such as separating a 64-kilodaltons (kDa) protein in a solution (250 sextillion times smaller). Magnetic power generators and sensors that place, move, stop and reverse paramagnetic particles by engineering design with torque, velocity or oscillating combinations are well characterized and employed throughout modern industrial, clinical and other scientific applications.

In turn, magnetic nanomaterials have also been applied to enhance diagnostic imaging capabilities as contrast agents in magnetic resonance imaging (MRI). These agents typically consist of a metal core with a biocompatible coating that intensifies image quality when exposed to the magnetic field. In this context, Raman spectroscopy and optical fluorescence imaging have been combined with intraoperative computational programs and robotics. While providing real-time navigation, models, and distance, angle, and volume measurements, this invention is incorporating novel magnetic nanomaterials as virtual scalpels that can improve surgical precision.

Technical Problem

Despite miniaturization, both minimally invasive and open surgery methods require a patient entry point or points, often through the peritoneum via trocar port. Introduction of one or more sleeve ports enables access for surgical tools like optics (e.g., cameras, light, etc.) and instruments (e.g., clamps, scalpels, scissors, etc.) routinely used to excise or repair organs and tissues. However, several ports are typically required to traverse X, Y and Z planes to allow 3D movement and control.

In many cases, manipulation of adjacent organs or tissues using a working port is also required. The sizes of working port incisions vary, but as with all ports for any purpose, they can pose risks of common complications from post-surgical pain and discomfort, to peri-optic bleeding, and infection. Scarring is also a concern, especially with young patients and those with dysmorphic disorders at any age.

Yet other surgical challenges may relate to non-invasive access and scale. Among these challenges traditionally requiring painstaking interventions in nearly inaccessible sites are the Bartholin's glands (e.g., abscesses or cyst removal), Cowper's gland (e.g., cyst or stones removal), eccrine and apocrine glands (i.e., acne vulgaris), Eustachian tubes, and lymph nodes. Another such example is the meibomian glands along the edge of the eyelid that account for dry eye disease affecting 20 to 90% of adult populations. The glands are closely packed, vertically spaced, and traverse a nearly perpendicular and linear path throughout the tarsal plates in both the upper and lower lids. A safe and reliable method to remove blockages would thus address an otherwise intractable problem with otherwise limited results from countless drops, prescription steroid and anti-inflammatory drugs, massages, warm compresses and ultrasound interventions.

Thus, to prevent or mitigate surgical risks and negative sequelae, new methods are needed to further reduce or avoid incisions for any purpose, from open-cavity procedures to minimally invasive methods, where elimination or use of fewer and/or smaller entry and working ports could be achieved.

Solution to the Problem

The present invention solves problems associated with surgical incisions for patients, as well as technical complications associated with procedural port incisions that restrict the operational field in minimally invasive methods. In the proposed invention, a magnetic fullerene fluid is injected and used as a "nanoparticle-scalpel" at the surgical site under external control for manipulation via magnetic fields using image guidance modalities.

The invention enables surgical intervention with access comparable to routine "needle biopsy" or "steroid injection" methods. This virtually eliminates incision and entry trauma, organ manipulation and consequent deleterious sequelae. The magnetic fullerene fluid would reduce surgeon technical limitations, tissue trauma and attendant pain and discomfort, notwithstanding a litany of common surgical complications, including opportunistic and occasionally life-threatening infections (e.g., methicillin-resistant *Streptococcus aureus*, MRSA). The technique would shorten the duration of procedures and thus anesthetization, thereby improving facility logistics in the short term and patient and healthcare cost outcomes in the long term. To the extent that patient discomfort and pain are directly proportional to incisions and secondary tissue manipulation, and where clinically appropriate, the method could also reduce or eliminate the need for general anesthesia with shorter procedures that could be managed under short-acting sedation. The fullerene and halogen functionalization would also impart microbiocidal activity in the presence of complicating pathogens.

The use of a magnetic field for establishing location is also flexible and convenient and does not require bulky equipment, nor is it impacted by blocking issues. A magnetic fullerene fluid can transfer real-time position information in the magnetic field to achieve the tracking and navigation of the nanoparticles. This can facilitate preoperative imaging, display surgical fields in real time, and track precise movement and rotation of surgical nanoparticles. Such robotic aids are inherently suitable for this alignment and stabilization task, which can reduce manual errors and complications arising from fatigue, limited dexterity and/or field of vision of the surgeon.

SUMMARY OF THE INVENTION

The principal embodiment of the invention is a magnetic fullerene fluid comprised of incompressible allotropes of carbon, or fullerenes, with electronic and magnetic properties, which presents a surgical tool to perform minimally invasive surgery via needle injection or anatomical placement for subsequent manipulation, movement, and rotation. This magnetic fullerene fluid thus serves as an atomic-scale scalpel to perform surgical procedures employing externally applied and precisely computer programmed magnetic fields.

In the preferred embodiment, the magnetic surgical fluid would include carbon fullerenes and their functional derivatives, preferably halogenated metallofullerenes. Inherent fullerene affinities include kinetic or electrical energy that create and reverse charges. Fullerene excitation results in particle movement and fullerene-to-fullerene contact when energized. Particle velocity and rotation under manipulation translates to a mechanical force upon contact with other matter, however, the fullerenes remain intact.

Complex functional arrangements and fullerene outer shell compatibility enable dual modification with halogen and magnetic matter in various stable configurations. Chemical functionalization of magnetic and rare-earth metals affixed to the outer carbon shell of the fullerene transforms it into an atomic-scale, magnetized particle that can be manipulated via magnetic fields. Further functionalization of the outer carbon shell with halogen particles then creates a halo fullerene with protruding halogen side chains that are caustic upon contact. The preponderance of the fullerene is thus comprised of inert surface carbon and electron orbitals with limited paramagnetic matter and halogen protrusions. Repeated halo fullerene and tissue contact results in microscopic scalding and protein melting to "polish" cellular matter at an atomic scale. The caustic aspect of the halogen side-chains seals and smooths cellular and venous vessels and capillaries through chemical cauterization with minimal trauma and absent the requisite thermal intensity of laser radiation. Like tissue cells, viral, bacterial and fungal pathogens are obliterated upon contact with energized fullerenes, which reduces the risk of opportunistic infection.

An object of the present invention is the application of an external magnetic field that is applied after insertion of the composition at the site in the patient anatomy. In the present invention, an external magnet, series of magnetic rings, or alternative magnetic configurations are used to manipulate the inserted magnetic fullerene fluid, magnetic nanoparticle suspension, or combination thereof at the site of injection or placement. In the proposed invention, an externally applied magnetic field is concentrated on a region containing magnetic nanoparticles inserted or injected via an instrument that is manually or robotically guided. Externally adjusting the magnetic field (e.g., rotating in space, changing intensity, switching on and off, etc.) results in the ability to change the path, velocity, torque and propulsion of the magnetic fullerene nanoparticles for surgical procedures. The magnetic fullerene nanoparticles are thus instantaneously propelled in 3D space using externally applied magnetic fields across X, Y, and Z-axes in nanometer increments. Using computational modeling and magnetic oscillation and pulsation, the fullerenes thus function as a quantum scale scalpel with unmatched incising, cutting, excision or pulverizing nanometer precision unattainable with conventional surgical tools or lasers.

The magnetic field assembly is controlled by a computer that simultaneously reads and patterns the images, tracks the nanoparticles, controls magnetic field intensity and direction, and provides real-time images of the target region throughout the procedure. In advance of nanoparticle injection, the targeted region is mapped to establish the appropriate concentration and type of nanoparticles for a given procedure. The computational capacity for instantaneous reversal of the magnetic field polarity and rotational movement of the robotic assemblies is coupled to incompressible atomic scale paramagnetic fullerene particles. This allows for exacting energy and precise magnetic manipulation via external force parameters to perform a surgical intervention in an anatomical field or target site.

In addition to precise excision applications, the magnetic fullerene fluid of the proposed invention can be applied to perform specific tasks through iterative rotations and micron axial positioning to polish dense structures effectively into atomic dust, e.g. a bone spur or damaged cartilage. Throughout surgery, intraoperative 3D models can be used to calibrate the magnetic field intensities, direction and calculate procedure duration. Thus, robotic guidance, spatial image mapping, and mathematical coordinate programing enable procedural automation without direct manipulation by the attending physician. Alternatively, some magnetic fullerene fluid techniques and magnetic field positioning could be performed using human guidance and physical positioning consistent with more traditional surgical instrument manipulation.

The nanoparticle scale of the proposed invention can also allow complex surgical procedures and enable interventions in nearly inaccessible targets, such as tiny glands, anatomical sacks, vesicles and passages that routinely require resurfacing or clearing. Examples might include endometriosis, bone spurs, blocked meibomian glands, and the need to excise tonsils or kidney stones. Thus, by exploiting precise, 3D images to avoid collateral tissue disruption and applying magnetic field mapping and algorithms, the proposed nanoparticle invention can perform unassisted robotic surgery as a safe, new paradigm of non-invasive interventions now addressed with both open-cavity and endoscopic or laparoscopic procedures. Following the procedure, the nanomaterials would be retrieved via a ceramic syringe by flushing the region of fullerenes and debris and/or collected via directional magnetic energy. With respect to tumors, debris and byproducts of fullerene activity could be removed during or upon completion of the procedure. Aspiration of the region can be accomplished using the same or a similar injection instrument, such as a double-lumen irrigation-suction tube. Given the size or density of the target (e.g., large, encapsulated breast fibroadenoma tumors), the magnetic fullerene fluid would pulverize the tissues into particulates with activated contact, whereby the external magnetic field could be polarized to separate the magnetic fluid from tissue debris and allow for iterative cycles of intra-procedural aspiration and surgical activation.

By illustration, the capabilities of the proposed invention would facilitate precise action on delicate surfaces, such as the ability to hollow out the core of microscopic objects (i.e., a cell) or macroscopic objects (i.e., an organ) without injury or affect to the outer membrane appearance or shape.

By further illustration, the proposed invention would perform microscopic incisions comparable to splitting a single human hair longitudinally into a dozen invisible strands.

Also described in the invention are methods for performing the minimally invasive surgical procedure. The methods generally comprise mapping the region of interest using traditional or contrast-enhanced MRI, ultrasound, or a combination of imaging methods, followed by the injection or placement of a calibrated volume containing one or more classes of nanoparticles into the target region and positioning an external magnetic field assembly around the surgical site or region of interest. Like atomic manipulation using a scanning tunneling microscope, whereby a single atom may be moved in space, the magnetic fullerene nanoparticles are capable of discrete rotational and axial movement at controlled velocities and directions governed by the external magnetic field, imaging modalities and computer-generated pattern to allow nanoscale surgery that achieves cellular-level accuracy. Conceivably, destroying a single cancer cell without harming an adjacent healthy cell is feasible given sufficient imaging capabilities and precise resolution.

BRIEF DESCRIPTION OF THE DRAWINGS

Many aspects of the present fullerene magnetic fluid composition can be designed. The components of the drawings are not intended to indicate scale, rather emphasis is placed on the structure of the fullerene and various types of fullerenes that may comprise the magnetic composition. Moreover, combinations of the fullerenes illustrated would be obvious to someone skilled in the art.

Figure 1:
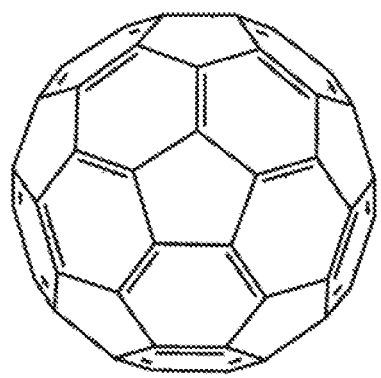
FIG. 1 is a molecular representation of a prototypical $C_{60}$ fullerene.

It would be obvious to one skilled in the art that the different sized pristine fullerenes with the chemical formula of $C_{60}$, as shown in FIG. 1, or $C_{70}$, $C_{76}$, $C_{78}$, $C_{80}$, $C_{82}$, $C_{84}$, as well as higher molecular-weight molecules, would impart similar function. More generally, the common production methods of fullerenes can be accomplished economically and at scale to generate differently sized fullerenes. It would also be obvious to one skilled in the art that any fullerene of $C_{2n}$, whereby n=10, 12, 13, 14, 15, . . . , 360 would provide similar characteristics. Likewise, it would be obvious that the combination of the endohedral fullerene of FIG. 3 with the functional side chains of FIG. 2 would impart similar action.

DETAILED DESCRIPTION OF THE INVENTION

The primary embodiment of the present invention is a magnetic surgical fluid comprised of a plurality of nanomaterials, preferably fullerenes, and more preferably halo metallofullerenes, for performing minimally invasive surgery. The method advances minimally invasive surgical techniques by injecting or inserting a magnetic fluid comprised of nanoscale fullerenes through a needle or proximal placement (i.e., an anatomical orifice) and then using an externally applied magnetic field to position and manipulate the fullerenes at the surgical site. Examples include surgical procedures associated with cellular or tissue extraction, vesselplasty, atherectomy, joint cavity resurfacing, or surgical techniques requiring extraction, excision, polishing, surfacing, or ablation. The method minimizes physical trauma and scarring and can be used to exenterate target tissues or cells, or resurface target sites. The dimensions specified in this disclosure are by way of example and are not intended to be limiting.

In one embodiment of the present invention, a magnetic fluid is comprised of a plurality of fullerene nanoparticles. Pristine fullerenes represent underivatized carbon structures of varying sizes comprised of pentagonal and hexagonal rings. The most common structure in this family is referred to as the buckminsterfullerene, which is comprised of 60-carbon molecules ($C_{60}$) in a truncated icosahedron structure. The approximate diameter of the outer cage of $C_{60}$ buckminsterfullerene is 1.1 nm and contains an internal hollow cavity 0.71 nm (~7 angstroms) in diameter. Another common fullerene molecule is the 70-carbon fullerene ($C_{70}$), an ellipsoidal-shaped structure comprising 37 faces (25 hexagons and 12 pentagons) and differs from $C_{60}$ through the equatorial insertion of 5 hexagonal faces. The structure of fullerenes is dependent on production techniques and parameters. Whereas the smallest possible fullerene composition is the dodecahedral ($C_{20}$), but fullerene structures that range from $C_{2n}$ to $C_{360}$, whereby n=10, 12, 13, 14, 15, . . . , 360, are common to production methods. Preferably, non-derivatized fullerenes of this invention include, but are not intended to be limited to, particle sizes of 200 nm and smaller.

In another embodiment of the present invention, a magnetic fluid is comprised of a plurality of functionalized fullerenes. Functionalized fullerenes, or fullerene derivatives, represent a specialized class of fullerenes, whereby the outer carbon cages of both pristine empty cage fullerenes and endohedral fullerenes are further modified via chemical functionalization of side-chain moieties. The use of specific chemical reactions results in diverse fullerene structures with different solubilities, size distributions and activities.

In one embodiment of the present invention, a fullerene cage is functionalized with multiple side-chain halogens (e.g., iodine, bromine, chlorine and fluorine) and transition or rare-earth metals. This halogenated metallofullerene (halo metallofullerene) is comprised of a fullerene shell of $C_{2n}$; whereby, n=10, 12, 13, 14, 15, . . . 360, such that multiple side-chain halogens and magnetic metals can be attached to the core carbon cage. Other functionalized fullerenes include the attachment of hydroxyl groups (—OH), as well as nucleophilic or pericyclic reactions, hydrogenation, oxidation, hydroxylation, electrophilic, carbene, or radical additions.

In another general aspect of the present invention, the nanoparticles are endohedral fullerenes, which are fullerenes that contain additional atoms, ions, or clusters within the cavity of the carbon cage. In the present invention, endohedral metallofullerene complexes may include nitride-fullerenes, metal carbide fullerenes, metal oxide fullerenes, metal sulfide fullerenes, metal hydrocarbide fullerenes, and metal carbonitride fullerenes. The intrinsic hollow interior of the fullerene enables entrapment or confinement during synthesis. Numerous approaches have been described that articulate endohedral fullerene production methods. In the present invention, an element or cluster of elements that possess ferromagnetic, antiferromagnetic, paramagnetic, superparamagnetic, and diamagnetic properties are capable of fullerene encapsulation. In addition to encapsulation methods, ion implantation synthesis methods using low energy (e.g., iron) ion beams have produced spectra consistent with stable and reliable iron-encapsulated fullerenes. In a preferred embodiment, the inclusion of three gadolinium ions inside a fullerene cage establishes a superparamagnetic property that has been exploited previously by the inventors as an MRI contrast agent.

In yet another preferred embodiment, ferromagnetic nanoclusters such as iron, cobalt, nickel and their alloys may be enclosed inside the fullerene cage, as has been described throughout a substantial body of work (Vander et al., 2000; Liang et al., 2000; Tomitat et al., 2000; Dosa et al., 1999; Babonneau et al., 1998; Harris et al., 1998; Saito et al., 1994; McHenry et al., 1994; Majetich et al., 1993). Ferromagnetic nanoclusters possess profound magnetic properties that have also demonstrated superiority to bulk metallics of the same molecules. The fullerene represents an ideal material for encapsulation because carbon is inert up to 300° C. (572° F.) and provides an impenetrable and protective shell for the enclosed material.

The preferred embodiment of the present invention is a magnetic fullerene fluid suspension comprised of a therapeutically appropriate fullerene concentration to perform surgical procedures. In a further general aspect, a non-fullerene-based nanoparticle comprised of a magnetic material ranging in size from 1 to 200 nm in various shapes and disparate chemical functionality components can be used. These materials include, but are not limited to, cobalt, nickel, and iron nanoparticles with paramagnetic, ferromagnetic, or superparamagnetic properties. These non-fullerene alternative embodiments may include other tunable and magnetic nanoparticles comprised of a magnetic material, and a chemical component with atomic functionality.

The diamagnetic, paramagnetic, superparamagnetic, and ferromagnetic nanoparticles include, but are not limited to, pristine fullerene molecules, functionalized fullerene derivatives, endohedral fullerene molecules, functionalized endohedral fullerene molecules, and combinations thereof, collectively referred to as fullerenes throughout. Non-fullerene based magnetic nanoparticles are imagined behaving similarly by someone skilled in the art and would be obvious as an alternative material. Implementation may include one or more of the materials described above. The fullerene magnetic fluid composition may further include adjusting the concentration of the nanomaterials relative to the intended surgical procedure.

Figure 2A:
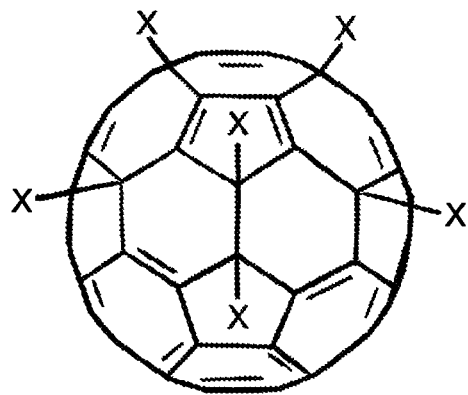
FIGS. 2A, 2B, and 2C are molecular representations of prototypical halo metallofullerenes of 60 carbon atoms functionalized with 4, 8, or 24 halogens and ferromagnetic transition and rare earth metals (X).
Figure 2B:
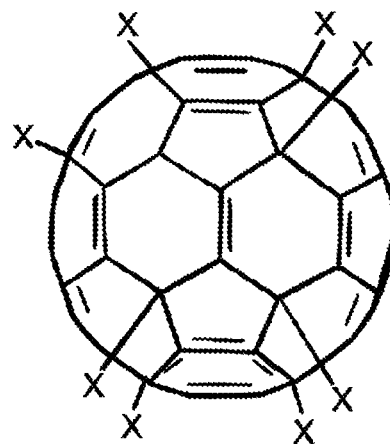
Figure 2C:
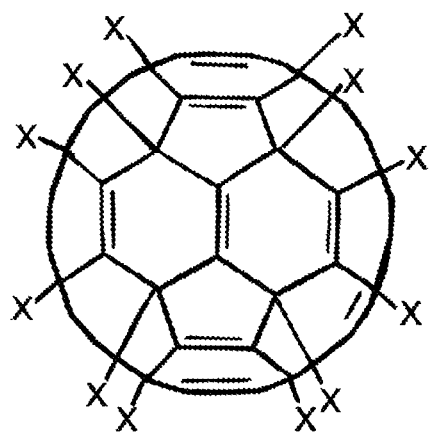
Figure 3:
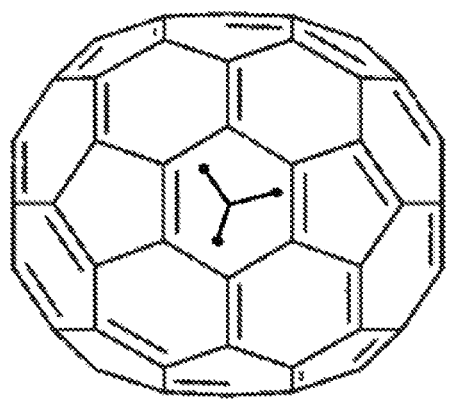
FIG. 3 is a molecular representation of a $C_{70}$ endohedral fullerene containing three paramagnetic molecules.

Embodiments of the present fullerene composition are detailed in FIG. 1, FIG. 2, and FIG. 3. FIG. 1 illustrates the structure of a pristine $C_{60}$ fullerene, FIG. 2 illustrates three conformations of a functionalized halo metallofullerene with the chemical formula of $C_{60}X_6$, $C_{60}X_8$, or $C_{60}X_{24}$, wherein X is a halogen selected from the group consisting of fluorine, chlorine, bromine, iodine and magnetic transition or rare-earth metals. FIG. 3 illustrates an endohedral fullerene containing a cluster of paramagnetic gadoliniums. In accordance with the images, variations such as different fullerene cages sizes that include $C_{70}$, $C_{76}$, $C_{78}$, $C_{80}$, $C_{82}$, $C_{84}$ and higher molecular weight molecules would be obvious by someone that is skilled in the art. Likewise, it would be obvious that an endohedral fullerene could be functionalized with a halogen or set of halogens sidechains as illustrated in FIG. 2.

The properties of the magnetic fullerene fluid differ from those of bulk material of similar molecules. Fundamentally, the magnetic fluid properties can be measured in nanometers allowing greater control, movement and manipulation. In the presence of an externally applied magnetic field, the fullerene fluid can be manipulated in vivo as well as transmit imaging characteristics that indicate their placement and the anatomy surrounding the target tissues.

In the preferred embodiment according to the present invention, a fullerene magnetic fluid, preferably comprising a plurality of halogenated fullerenes, halogenated endohedral fullerenes, magnetically functionalized fullerenes, or some combinations thereof are injected into a patient via traditional or flexible syringe, infusion needle, flexible cannula, or a catheter. Robotically steered needles are capable of precision steering and flexibility that can be microscopically manipulated around organs and tissue to reach a defined subsurface region in the patient, thereby minimizing consequent trauma. In the present invention, the delivery and method for injection of a fullerene magnetic fluid is dependent on depth, trajectory, and the specific biological parameters of the surgical intervention. Ideally, the delivery instrument would be comprised of a non-magnetic material (i.e., ceramic, removing the potential for interference with external magnetic fields or magnetic properties of the fluid material). In the present invention the fullerene magnetic fluid is thus introduced at a specific, desired site such as a tissue target via an instrument that is manually or preferably, robotically guided.

Upon injection of the fullerene magnetic fluid at the surgical site, the injection device may be removed or retracted temporarily. The injection instrument may also be used to recover the nanoparticles comprising the fullerene magnetic fluid upon procedure completion. The same injection instrument may likewise be used to flush the target region, as well as retrieve debris, cell fragments or other by-products associated with the procedure.

In another aspect of the present invention, the fullerene magnetic fluid is capable of introduction through an anatomical orifice without the use of a syringe or similar injection instrument whenever needle penetration is not necessary. Once introduced through an external opening, aperture, orifice or otherwise any patient anatomical entry, an externally controlled magnetic field would then direct the trajectory of the fluid and nanoparticles' movement into the patient. In the case of the present invention, an example of such an application would be a therapeutic concentration of the fullerene magnetic fluid positioned manually, or preferably robotically, in alignment with meibomian glands in the upper and lower eyelids using precision image guidance to treat dry eye by removing exudates from these tiny glands averaging from 2.0 to 5.5 mm in length.

In another general aspect of the invention, computerization and imaging systems would guide the nanoparticle procedure by programming the magnetic field parameters in three dimensions. Near-infrared fluorescence is one such imaging tool that has been commonly utilized in oncology procedures. Other imaging modalities, such as ultrasound and x-ray fluoroscopy, have also been utilized in removal of tumors and malignant tissues, albeit with some drawbacks, including field-of-view and ionizing radiation exposure. Intraoperative near-infrared fluorescence techniques have high photon penetration capabilities (into and out of living tissue) and high signal to background ratios due to low tissue autofluorescence in the 700-900 nm spectra. Applications of near-infrared fluorescence techniques also include engineered particles that target cancer cells and allow for high resolution, real-time visualization. Similarly, the combination of multiple targeting fluorophores can be leveraged to visualize any area or structures within the surgical field. Intraoperative fluorescence techniques are thus applicable for numerous surgeries including, but not limited to, lymph nodes, breast and brain tumors, and colon cancer.

A combination of pre-operative images and real-time intra-operative images that overlay the spatial positioning of the fluid contained magnetic fullerenes is used to track, position and monitor surgical action at the defined target region in order to ensure complete target tissue removal. In one general aspect, a static image of the region is overlayed with a real-time imaging modality. In the case of cancer, the real-time imaging modality is capable of visually differentiating cancer target cells from surrounding tissues. Fullerene tracking and trajectory are further overlaid; fluctuations in the external magnetic source can then be used to position, rotate, spin, and project the fullerenes over a defined course at a specific rate. The imaging modalities would provide real-time information to the surgeon and the computational guidance and manipulation system throughout the procedure. Whereby visualization of the targeted and highlighted cells would change over time as the target tissue and cells were destroyed or eradicated by the fullerenes. Given the eventual absence of target tissue visualization upon completion, the fullerene fluid could be collected by a similar injection instrument. The region and any debris could be similarly collected and flushed at the conclusion of the procedure.

In another general aspect, calculation of the magnetic field strength, positioning, and rotation are executed from at least one computer device that transfers information to the robotic arm and magnetic array. Each command is executed based on pre-operative image modeling instructions, real-time intra-operative imaging modalities, magnetic fullerene fluid tracking, and combinations thereof, transmitted by the computer device or system. In a preferred method of the present invention, the surgical region is analyzed prior to the procedure, whereby precise coordinates, topography, and tomography are recorded and used to spatially guide the robotics and magnetic sources. In other embodiments, the surgical table can be rotated, lifted, tilted or maneuvered independently from the computer device or systems. Additionally, cloud computing and supercomputing systems and connectivity opportunities are pervasive and would be applicable to all techniques associated with the present invention.

Upon the injection, placement, or other introduction of the fullerene magnetic fluid composition to the target site, a variable, controlled external magnetic field would be applied throughout the surgical procedure. In addition to presurgical imaging and site mapping, intraoperative real-time fluorescence-guided imaging techniques may be used in a variety of procedures, as well as during tumor resection for margin evaluation, ensuring complete excision, and minimizing healthy tissue damage. Subjecting the composition of the present invention to a controlled magnetic field enables molecular manipulation of the magnetic nanoparticles.

Magnetic manipulation includes precise movement, orientation, positioning, rotation, spinning, or some combination of magnetically induced propulsion of the magnetic nanoparticles at or around a target site or region. As such, interactions of the fullerene magnetic fluid and the external magnetic field provides a virtually non-invasive surgical technique. Applications would include but not be limited to precise excision of solid tumors, angioplasty, or clearing obstructions or other debris from any bodily cavity. The technique would thus offer an alternative to traditional surgical procedures, ensure hemostasis, and provide nanoscale dimensionality at a targeted surgical site.

In certain embodiments, the magnetic field source is configured to include two or more magnetic field sources, whereby 4, 6, 8, 10, or more magnetic field sources can be positioned and rotated independently. The magnetic fields can be arranged to have multiple field sources combine or oppose each other to control direction, velocity, and motion. In the preferred method of the present invention, the magnetic field sources are arranged in various placements relative to each other. Each magnetic field source can be switched on and off independently, collectively, and freely throughout. The magnetic field sources may be aligned relative to another magnetic field source to increase field strength or arranged such that two fields oppose each other to effectively suspend or to rotate the fullerenes by revolving the magnetic field sources or oscillating source emissions.

The magnetic field sources arrangement can also be configured in rectangular, triangular, circular, pentagonal, as well as other geometric configurations and combinations depending on the procedure. In certain aspects, the magnetic field source may be linear or focused at the end of a wand or arm. The positioning, array and number of magnetic poles in each array may also vary between applications.

The use of a controllable magnetic field and space enables control over a "zero-dimensional" fullerene or numerous particles simultaneously. The magnetic fluid properties allow the instantaneous ability to impart or suspend fullerene movement in 3D, as well as start and stop fullerene rotation by effectively turning a circuit on and off.

The fullerene thus acts as a virtual semiconductor material using polarity and external magnetic field emissions to manipulate a binary set of operations represented as on/off states and analyzed with algebraic Boolean operators, which are "and, or, not." Whereby "and" defines movement and rotation; "or" defines movement or rotation; and "not" defines zero movement and zero rotation, or a stationary object. The logic properties are similarly observed in magnetic polarities, as with a switch that is either opened or closed, or by a binary description a 0 or 1. Conversely, magnetic assemblies that guide the fullerenes can oppose each other to establish a theoretical "third switch," whereby the on position of one magnetic field may oppose the on position of a second magnetic field, counteracting and nullifying each other via polarity.

Greater control could also be realized through magnetic arrays that alter polarity through rotation. Whereby, the rotation speed can present variable poles at a defined speed, thereby switching the binary operators in rapid succession to transfer tremendous torque to the fullerene while suspended, without turning the field array on and off. Principally, the fullerene is contained inside the rotational magnetic array at some distance, as a relative radius, because the point of the fullerene does not require precise equidistant alignment inside the circumference of the circular array. Rotation of a circular array exerts a specific magnetic field at different coordinates along its circumference. The magnets can be positioned and rotated in a desired polarity across the arc, and the speed of rotation can be varied to apply differing magnetic fields. These unique features establish a virtual atomic scale semiconductor operating without a structural and stationary platform, as in silicon wafer confinement.

In the preferred method of the present invention, the magnetic source or magnetic sources of variable geometries, sizes, positioning, poles, rotation, strength, and speed can be controlled in accordance with the depth of the target site within the patient's body and size of the target region. In the preferred method of the present invention, the magnetic source or magnetic sources are external to the patient and can be used to control movement, torque, rotation, and/or extracorporeal manipulation of the magnetic fluid containing fullerenes without mechanical contact.

In the preferred embodiment of the present invention, the fullerene magnetic fluid can also transmit force from an externally applied magnetic source to selectively rupture individual cells. The diameter of the fullerene is between ~1 and 20 nm depending on its structure and functionality. The scale creates a fine resolution and sharp tip for penetrating and rupturing cell membranes with minimal force. Similar to the sharp tips of atomic force microscopy (AFM) cantilevers, the fullerene can induce multiple consecutive indentations on the cell membrane with minimal force (nano Newtons, nN). Likewise penetration, tunneling, and rupture of the membrane can be achieved with small diameter nanoparticles at relatively low forces of less than 0.5 Newtons. The combined small diameter of the fullerene and tunable magnetic fields can produce force ranges beyond the structural modulus of cell membranes to allow penetration. In another aspect of the present invention, the externally applied magnetic field can rotate to induce spin and torque to the fullerenes for use as mechanically abrasive nanoparticles. In this general aspect, the abrasive surface of the fullerene cage and functional groups (side chains) apply an ablative force to the target region that can rupture cells and polish surfaces.

In a preferred method of the present invention, the magnetic field sources require precision guidance in both time and space; thus, human manipulation would not be feasible. The magnetic field source and assemblies can be configured in a variety of ways depending on the procedure and driven by one or more robotic arms or carriages controlled by at least one computer processing instructions from the imaging modality. The end magnetic source arrangements can thus freely rotate, pivot, and tilt at controllable speeds. Both the arms and the magnetic sources can receive simultaneous instructions from the computer device and system that allow for two or more units to work separately or independently. For instance, the arm can move in one plane across a defined area while the field rotates around it. This would enable the fullerenes contained in the magnetic fluid to spin at a defined rate, as imparted by the speed of the rotating magnetic source, as well as move along a defined path across the site. In the present invention it is obvious that the robotics and the magnetic sources can freely move in a defined direction at a defined speed as programed by the computer device or systems.

Depending on the type of procedure, different magnetic source arrangements, shapes and sizes can be attached to the robotics. In the present invention, the magnetic source arrangements refer to the spacing, polarity, and distribution of the magnets across the source. Magnetic arrangements can include but are not limited to Helmholtz assemblages and Hallbach arrays. In some embodiments, a concentrated magnetic field can also be placed at the end of a wand.

In a general aspect of the present invention, the fullerene fluid is capable of magnetic aggregation and removal via syringe or similarly minimally invasive implement following the surgical procedure. The injection instrument is thus capable of retrieving the inserted magnetic nanomaterial fluid, as well as flushing the target site to remove debris or matter resulting from the mechanical action of the fullerenes on cells, tissues, etc. during the procedure.

While the preferred embodiments of the present invention and methods have been described in reference to the surgical environments and procedures for which they were designed, they are intended only to illustrate the principles of the present invention concepts. Modification or combinations of the above-described compositions, other embodiments, and configurations for carrying out the invention, and variations of aspects of the invention that are obvious to those skilled in the art are intended to be within the scope of the claims.

We claim:

1. A magnetic surgical fluid composition comprising fullerene nanoparticles and an inert fluid that physically and mechanically destroys a biological target through the application of an external magnetic field, wherein the fullerene nanoparticles comprising one or more of the following:
   a. halogen-functionalized metallofullerenes,
   b. halogen-functionalized metalloendohedral fullerenes, having the chemical formula of $C_{60}X_6$, $C_{60}X_8$, or $C_{60}X_{24}$, wherein X is a halogen selected from the group consisting of fluorine, chlorine, bromine, and iodine, wherein the fullerene nanoparticles destroy, rupture, micronize, resurface, excise, ablate or polish a defined region using external magnetic fields.

2. The magnetic surgical fluid composition according to claim 1 that is injected into a patient at a target site.

3. The magnetic surgical fluid composition according to claim 1 that is placed proximal to an orifice, cavity, or opening at a target site.

4. The magnetic surgical fluid composition of claim 1, whereby the fullerene nanoparticles may be ferromagnetic, paramagnetic, superparamagnetic, or combinations thereof.

5. The magnetic surgical fluid composition of claim 1, whereby the fullerene nanoparticles are administered at a therapeutically relevant dose and concentration.

6. The magnetic surgical fluid composition of claim 1, wherein the inert fluid is either hypotonic, hypertonic, or isotonic.

7. The magnetic surgical fluid composition of claim 1, wherein the fullerene nanoparticles are doped with a magnetic transition metal.

8. The magnetic surgical fluid composition of claim 1, wherein the fullerene nanoparticles contain one or more magnetic clusters enclosed with the inner sphere of the fullerene.

9. The magnetic surgical fluid composition according to claim 1 that is controlled by an external magnetic field assembly that can be configured, rotated, and positioned to alter distance, location, magnitude, direction and strength of the magnetic field.

10. The magnetic surgical fluid composition according to claim 1 that is controlled by a magnet, magnetic wand or array of magnets spatially configured to align, freely rotate and position directionally around the target region.

11. The magnetic surgical fluid composition according to claim 1 that can be visualized by an external imaging device, imaging processor, tracking system, navigation processor, and one or more display devices.

12. The magnetic surgical fluid composition according to claim 1 that can be visualized by radiography, magnetic resonance imaging (MRI), computed tomography (CT), fluoroscopy, ultrasound, echocardiography, positron emission tomography (PET), or another appropriate medical imaging device.

13. The magnetic surgical fluid composition according to claim 1 that is controlled, manipulated, and position robotically by a magnetic field outside of the patient and without human manipulation.

14. The magnetic surgical fluid composition according to claim 1, wherein the biological target is a surgical site associated with cellular or tissue extraction, vesselplasty, joint cavity resurfacing, or alternative surgical techniques requiring extraction, excision, polishing, surfacing, clearing, unblocking, or ablating a surgical target.

* * * * *